United States Patent [19]

Terashima et al.

[11] Patent Number: 5,673,814
[45] Date of Patent: Oct. 7, 1997

[54] ELEMENT PRESSING MECHANISM FOR DRY CHEMICAL ANALYSIS ELEMENT CARTRIDGE

[75] Inventors: Kaoru Terashima; Sigeru Tezuka, both of Saitama-ken, Japan

[73] Assignee: Fuji Photo Film Co., Ltd., Kanagawa-ken, Japan

[21] Appl. No.: 596,078

[22] Filed: Feb. 6, 1996

[30] Foreign Application Priority Data

Feb. 7, 1995 [JP] Japan ................................. 7-018969

[51] Int. Cl.⁶ ................................................. B65H 1/08
[52] U.S. Cl. ................................................ 221/227; 221/232
[58] Field of Search ................................ 221/226, 227, 221/232, 238, 279, 268, 211, 210

[56] References Cited

U.S. PATENT DOCUMENTS

| | | | |
|---|---|---|---|
| 4,187,077 | 2/1980 | Covington et al. | 422/63 |
| 5,056,764 | 10/1991 | Mochizuki | 267/291 |
| 5,271,896 | 12/1993 | Jakubowicz et al. | 422/63 |

FOREIGN PATENT DOCUMENTS 0567067  10/1993  European Pat. Off. .

*Primary Examiner*—Kenneth Noland
*Attorney, Agent, or Firm*—McAulay Fisher Nissen Goldberg & Kiel, LLP

[57] ABSTRACT

In a chemical analysis element cartridge, chemical analysis element pressing mechanism is inserted into a cartridge body to press a stack of chemical analysis elements in the cartridge body toward an element take-out port formed in one end of the cartridge body. The element pressing mechanism includes a stopper to be engaged with an engagement teeth formed on an inner wall surface of the cartridge body and a pressing member which presses the stack of the chemical analysis elements toward the element take-out port under the force of a coiled spring. The stopper has a slider member which is slidable relative to a shaft portion of the pressing member and the coiled spring is disposed around the slider member with its one end in abutment against the pressing member and its the other end retained by a spring retainer portion formed on one end of the slider member. A bulged portion on the outer surface of the slider member aligns an effective center of an envelope defined by the end of the coiled spring with the effective center of the spring retainer portion.

4 Claims, 8 Drawing Sheets

ELEMENT PRESSING MECHANISM FOR
DRY CHEMICAL ANALYSIS ELEMENT
CARTRIDGE

BACKGROUND OF THE INVENTION

1. Field of the Invention

This invention relates to a dry chemical analysis element cartridge in which a plurality of dry chemical analysis elements each having a reagent layer whose optical density changes upon chemical reaction, biochemical reaction or immunoreaction with a specific biochemical or chemical component contained in a sample liquid such as blood or urine are stored and taken out one by one, and more particularly to an element pressing mechanism for such a dry chemical analysis element cartridge.

2. Description of the Related Art

There has been put into practice a dry ("dry-to-the-touch") integrated multi-layered chemical analysis film with which the concentration or activity of a specific chemical component or the concentration of a solid component in a sample liquid can be quantitatively analyzed by only spotting a droplet of the sample liquid onto the film. Further, a dry chemical analysis film which is formed of filter paper and has one or more layer has been proposed and partly put into practice.

When quantitatively analyzing the chemical components or the like contained in a sample liquid using such a chemical analysis film, a droplet of the sample liquid is spotted onto the film (on the spreading layer when the film is provided with a spreading layer and directly on the reagent layer when the film is not provided with a spreading layer) and is held at a constant temperature for a predetermined time (incubation) in an incubator so that coloring reaction (coloring substance generating reaction or color change reaction of the coloring substance in the reagent layer) occurs, and the optical density of the color formed by the coloring reaction is optically measured. That is, measuring light containing a wavelength which is preselected according to the combination of the component to be analyzed (sometimes will be referred to as "analyte", hereinbelow) and the reagent contained in the reagent layer of the film is projected onto the film and the optical density of the film is measured. Then the concentration or the activity of the analyte is determined on the basis of the optical density using a calibration curve or a standard curve which represents the relation between the concentration (content) of the analyte and the optical density.

The integrated multi-layered chemical analysis film generally comprises a support sheet of organic polymer or plastic and at least one reagent layer formed on the support sheet. Preferably a spreading layer is formed over the reagent layer. The chemical analysis film is generally in the form of a film chip of a predetermined shape such as square or rectangle. The film chip is sometimes provided with a frame of organic polymer or the like for facilitating automated handling of the film chip and sometimes used as it is without frame. The chemical analysis film with a frame is generally referred to as "a chemical analysis slide" and that without frame is generally referred to as "a frameless chemical analysis film".

In this specification, the term "chemical analysis element" should be broadly interpreted to include the frameless chemical analysis film, the chemical analysis slide and the single-layered or multi-layered chemical analysis film formed of filter paper (with or without frame) as well as an electrolyte analysis slide for quantitatively analyzing the activity of particular ionic substances contained in a sample liquid and other like elements and devices for various analyses. We have proposed a technique for loading a plurality of frameless chemical analysis films directly in a cartridge, setting the cartridge in film supplier of a biochemical analysis apparatus and taking the frameless chemical analysis films one by one from the cartridge for use in analysis.

For example, in a chemical analysis element cartridge disclosed in Japanese Utility Model Publication No. 57(1982)-53271 (U.S. Pat. No. 4,151,931), a plurality of chemical analysis elements are stored in a stack in the cartridge and the uppermost chemical analysis element is pushed outward through a take-out port formed in one side of the upper portion of the cartridge by a pusher blade which is moved in the transverse direction of the cartridge. In the cartridge, the stack of the chemical analysis elements are supported on a support member which is incorporated in the cartridge body by way of a ratchet mechanism to be movable only upward and the support member is pushed upward by a plunger to bring the second uppermost chemical analysis element to the take-out port each time one chemical analysis element is pushed out.

Further there has been disclosed a technique in which the stack of chemical analysis elements are pressed toward the take-out port by a pressing member which is urged by a coiled spring and the chemical analysis elements are taken out through the take-out port one by one. For example, see Japanese Unexamined Patent Publication No. 5(1993)-188058, Japanese Unexamined Patent Publication No.1 (1989)-87438 (EP No. 0 304 838A) and EP No. 0 567 067A.

In the conventional chemical analysis element cartridge, a element pressing mechanism comprising a pressing member and a coiled spring must be provided behind the stack of chemical analysis elements, and the coiled spring must have a length corresponding to the height of the stack of the chemical analysis elements, which can cause trouble when incorporating the element pressing mechanism in the cartridge body.

That is, as shown in FIG. 11, when the element pressing mechanism b is inserted into the cartridge body a from one end thereof toward a stack of chemical analysis elements in the cartridge body a, the coiled spring e compressed between the pressing member (not shown) and the spring retainer d1 of the stopper d is apt to bend and the center of the outer end portion of the coiled spring is moved away from the longitudinal axis of the spring, whereby a part of the spring projects outward beyond a corner of the spring retainer d1 and is caught between the cartridge body a and the spring retainer d1 to prevent insertion of the stopper d. This makes it impossible to bring the ratchet claws d2 into engagement with the ratchet teeth formed on the inner surface of the cartridge body a, and assembly of the cartridge must be try again, which results in a great deterioration of working efficiency. Especially when a part of the coiled spring is caught between the cartridge body a and the spring retainer d1 with ratchet claws d2 in engagement with the ratchet teeth, it is very difficult to disengage the ratchet claws d2 from the ratchet teeth.

SUMMARY OF THE INVENTION

In view of the foregoing observations and description, the primary object of the present invention is to provide an element pressing mechanism for a chemical analysis element cartridge in which the end of the coiled spring on the side of the spring retainer of the stopper is prevented from projecting outside a flat (rectangular or square) seat of the spring retainer at any one of the corners of the seat, whereby assembly of the chemical analysis film cartridge is facilitated.

A chemical analysis element pressing mechanism in accordance with the present invention is for a chemical analysis element and is inserted into a cartridge body to press a stack of chemical analysis elements in the cartridge body toward an element take-out port formed in one end of the cartridge body. The element pressing mechanism comprises a stopper to be engaged with an engagement means formed on an inner wall surface of the cartridge body and a pressing member which presses the stack of the chemical analysis elements toward the element take-out port under the force of a coiled spring. The stopper has a slider member which is slidable relative to a shaft portion of the pressing member which is disposed in the cartridge body to be slidable toward and away from the stack of the chemical analysis element on the side of the stack remote from the element take-out port and the coiled spring is disposed around the slider member with its one end in abutment against the pressing member and its the other end retained by a spring retainer portion formed on one end of the slider member. An aligning means which aligns an effective center of an envelope defined by said the other end of the coiled spring with the effective center of the spring retainer portion is provided on the outer surface of the slider member and/or the coiled spring.

When the coiled spring is substantially annular in a cross-section taken along a plane normal to its longitudinal axis, the aligning means may comprise a limiting portion which is in the form of a bulged portion formed on the outer surface of the slider member.

Further the effective center of the coiled spring may be aligned with the center of the spring retainer portion by changing the shape of the coiled spring 18. For example, in the case of a coiled spring which is substantially annular in a cross-section taken along a plane normal to its longitudinal axis, its effective center can be aligned with the center of the spring retainer portion by making smaller the diameter of the spring at one end than that in any other portion of the spring. Further the effective center of the coiled spring can be aligned with the center of the spring retainer portion by shaping the spring to be a rectangle or a square having rounded corners in cross-section.

In the chemical analysis element pressing mechanism in accordance with the present invention, the aligning means prevents the coiled spring from largely moving laterally, whereby the end of the coiled spring is prevented from projecting outside the spring retainer portion at any one of the corners of the spring retainer portion when the chemical analysis element pressing mechanism and is inserted into the cartridge body and fear of the coiled spring being caught between the stopper and the cartridge body. Thus assembly of the chemical analysis element cartridge is facilitated and the chemical analysis element cartridges can be assembled with a high efficiency.

DESCRIPTION OF THE PREFERRED EMBODIMENT

Figure 1:
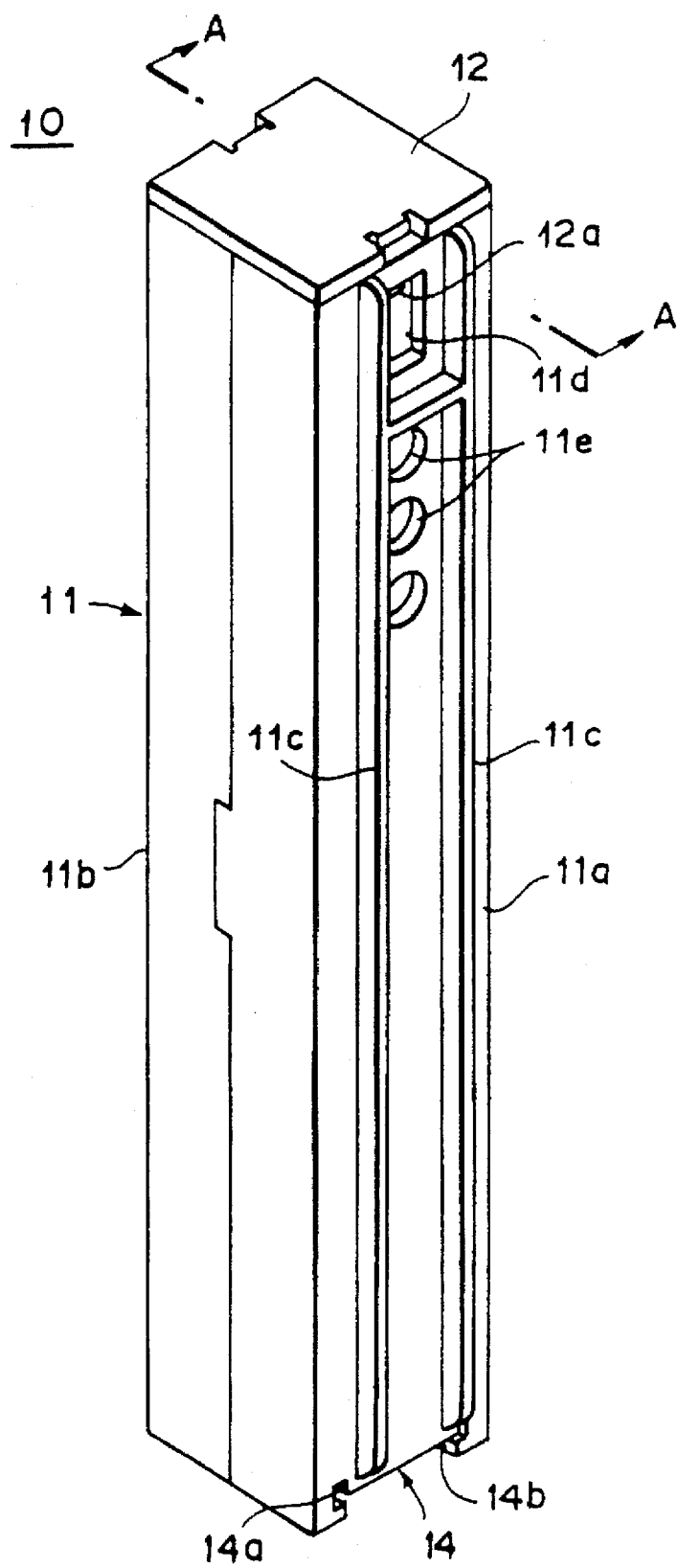
FIG. 1 is a perspective view of a chemical analysis film cartridge provided with a film pressing mechanism in accordance with an embodiment of the present invention.

In FIG. 1, a chemical analysis film cartridge 10 comprises rectangular cartridge body 11 formed of left and right halves. The upper end of the cartridge body 11 is open and a stack of frameless chemical analysis films 1 is loaded in the cartridge body 11. The upper end of the cartridge body 11 is closed by a lid member 12.

Figure 8:
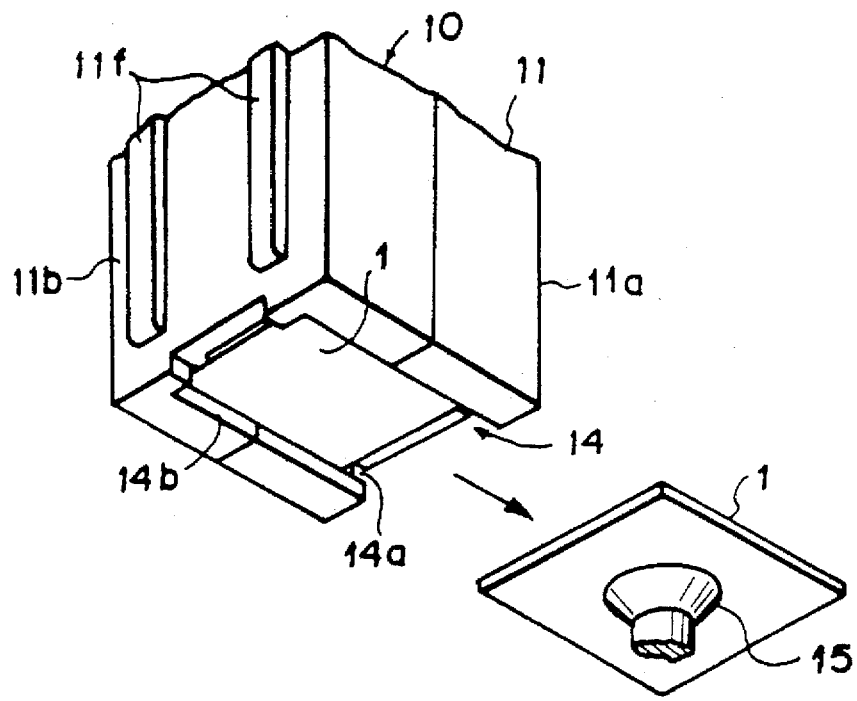
FIG. 8 is a cross-sectional view of the cartridge showing the manner of taking the chemical analysis film from the cartridge shown in FIG. 1.

A film take-out port 14 for taking out the chemical analysis film 1 is formed at the lower end of the cartridge body 11. The film take-out port 14 comprises a first opening 14a formed in one side wall 11a of the cartridge body 11 and a second opening 14b formed in the bottom of the cartridge body 11. Only one frameless chemical analysis film 1 can pass through the first opening 14a at one time. A film take-out suction pad 15 (FIG. 3) is inserted into the cartridge body 11 through the second opening when taking out the film 1. As clearly shown in FIG. 8, the second opening 14b communicates with the first opening 14a at the lower end of the side wall 11a of the cartridge body 11.

The thickness of the chemical analysis film 1 differs depending on its analyte and accordingly, the size of the first opening 14a is set depending on the thickness of the chemical analysis film 1 to be loaded in the cartridge body 11 so that the films 1 can be surely taken out one by one through the first opening 14a.

A film pressing mechanism 16 (FIGS. 2 to 6) for urging the stack of the chemical analysis films 1 toward the film take-out port 14 is provided in the cartridge body 11. The film pressing mechanism 16 comprises a pressing means 17 having pressing member 17a which is slidably received in the cartridge body 11 and is brought into contact with the stack of the chemical analysis films 1 on the side remote from the film take-out port 14 to press the stack of the films 1 toward the film take-out port 14, a coiled spring 18 which is for urging the pressing member 17a toward the film take-out port 14 and is substantially annular in a cross-section taken along a plane normal to its longitudinal axis, and a stopper 19 which carries the upper end of the coiled spring 18 and is engaged with the cartridge body 11 to suppress movement of the spring 18 away from the take-out port 14.

A pair of longitudinal ribs 11c are formed on said one side wall 11a of the cartridge body 11 spaced from each other in the transverse direction of the cartridge body 11. An opening 11d for holding a leg 12a of the lid member 12 and three distinguishing openings 11e are formed in the side wall 11a between the ribs 11c. The distinguishing openings 11e are initially in the form of a recess and has a thin bottom wall. For example, during assembly of the chemical analysis film cartridge 10, one of the distinguishing openings 11e is selectively opened depending on the thickness of the chemical analysis film 1 to be loaded in the cartridge 10. Ratchet teeth 11h (FIG. 3) is formed on the inner surface of the side wall 11a to extend in the longitudinal direction of the cartridge body 11 on each side of the side wall 11a.

A pair of longitudinal ribs 11f are formed on the side wall 11b opposed to the side wall 11a spaced from each other in the transverse direction of the cartridge body 11. An opening 11d for holding a leg 12a of the lid member 12 and an elongated through hole 11g which is opposed to said three distinguishing openings 11e are formed in the side wall 11b between the ribs 11f. Ratchet teeth 11h (FIG. 3) is formed on the inner surface of the side wall 11b to extend in the longitudinal direction of the cartridge body 11 on each side of the side wall 11b.

Though the cartridge body 11 is molded in two halves, the halves are fusion-bonded to one piece when the films 1 are loaded therein and cannot be parted thereafter though a parting line appears in FIG. 1. On the side surface where the parting line appears, there is provided a data recording portion (not shown) on which bar codes or the like representing the production lot, analyte, period of service, properties and the like of the chemical analysis films 1 loaded in the cartridge body 11 are recorded.

The structure of the film pressing mechanism 16 will be described in detail with reference to FIGS. 4, 5A, 5B and 5C, hereinbelow.

The pressing means 17 comprises said pressing member 17a in the form of a flat plate and a shank portion 17b in the form of a rectangular column which projects from the pressing member 17a perpendicular thereto. The shank portion 17b is a rectangle having rounded corners in cross-section and has a holding portion 17c at the free end portion thereof. When the pressing means 17 is incorporated with a stopper 19 to be described later, the holding portion 17c projects through the stopper 19. The holding portion 17c is provided with an opening 17d. Grooves 17e are formed on the side surfaces of the shank portion 17b. By virtue of the grooves 17e, the shank portion 17b which is of organic polymer can be molded straight in a uniform thickness.

The stopper 19 comprises a slider portion 19a which extends in the longitudinal direction of the cartridge body 11, is rectangular in cross-section and slidably receives the shank portion 17b of the pressing means 17, a spring retainer portion 19b which transversely extends at one end of the slider portion 19a and bears one end of the coiled spring 18 and an engagement portions 19c formed on the spring retainer portion 19b.

The slider portion 19a is shorter than the distance between the pressing member 17a and the holding portion 17c of the pressing means 17. That is, the shank portion 17b is longer than the distance between the spring retainer portion 19b of the stopper 19 and the pressing member 17a of the pressing means 17 in a state where the coiled spring 18 is compressed between the spring retainer portion 19b and the pressing member 17a to a predetermined extent and the holding portion 17c projects upward above the upper surface of the spring retainer portion 19b in the state. The minimum distance between the spring retainer portion 19b and the pressing member 17a depends upon the length of the slider portion 19a or the minimum compressible length of the coiled spring 18.

The stopper 19 is engaged with the cartridge body 11 to be movable relative to the cartridge body 11. That is, the engagement portions 19c are in the form of resiliently deformable thin plates which extend upward from opposite sides of the spring retainer portion 19b diverging away from each other and ratchet claws 19d are formed on the free end of each engagement portion 19c to project outward. The ratchet claws 19d are engaged with the ratchet teeth 11h on the inner surface of the cartridge body 11 as described above.

The slider portion 19a of the stopper 19 is provided on the outer surface thereof limiting portions 19e which function as an aligning means which aligns the center of the circular envelope defined by the end of the coiled spring 18, which is fit on the slider portion 19a and is compressed and stretched along the slider portion 19a, with the effective center of the spring retainer portion 19a and limits the movement of the coiled spring 10 so that the envelope cannot be outside the corners of the spring retainer portion 19b. The envelope is defined as a circle obtained by joining the outermost points on the end of the coiled spring 18 when the end of the coiled spring 18 moves laterally in all directions until it abuts against the slider portion 19a or the limiting portion 19e and is prevented from further moving in the direction.

Figure 6:
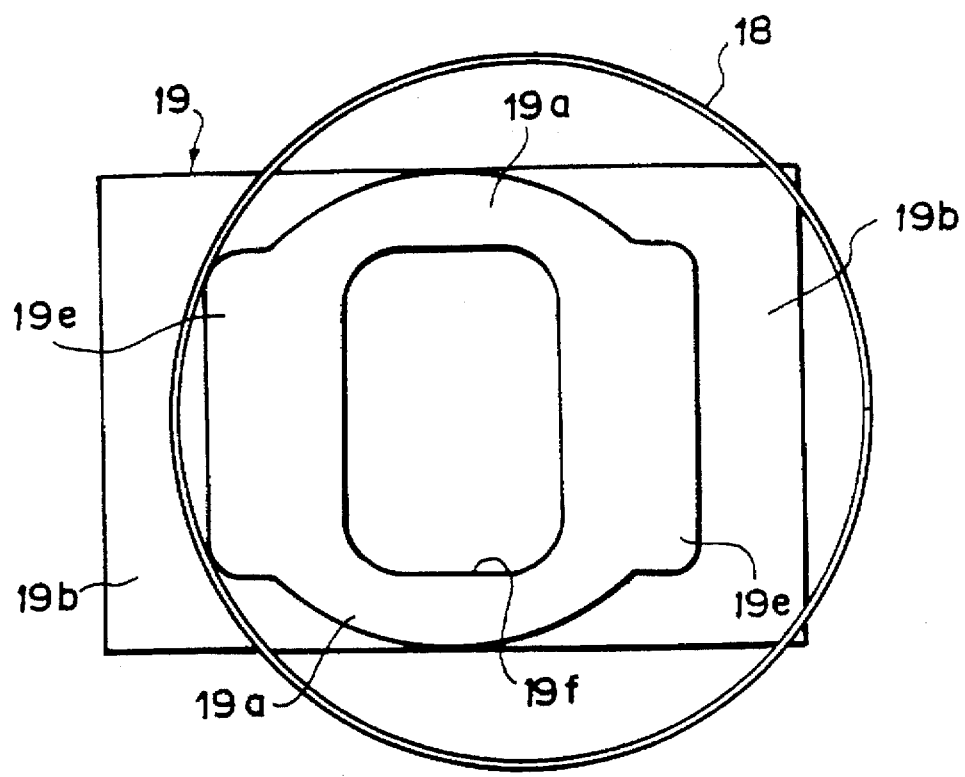
FIG. 6 is a bottom view showing the stopper and the coiled spring of the film pressing mechanism.

In this particular embodiment, the passage 19f in the slider portion 19a into which the shaft portion 17b inserted is an elongated rectangle in cross-section as shown in FIG. 6 and the limiting portions 19e are in the form of bulged portions formed on the slider portion 19a along the longer sides of the passage 19f. The amount of bulginess of the limiting portions 19e is set so that the distance between each of the corners of the spring retainer portion 19b, which is rectangular, and the point on the slider portion 19a diagonally opposed to the corner on the side remote from the corner is larger than the diameter of the coiled spring 18 and even if the center of the coiled spring 18 is moved away from the center of the spring retainer portion 19a by a maximum distance (until the coiled spring 18 abuts against the slider portion 19a), the coiled spring 18 cannot be outside any one of the corners of the spring retainer portion 19b as shown in FIG. 6.

Figure 7:
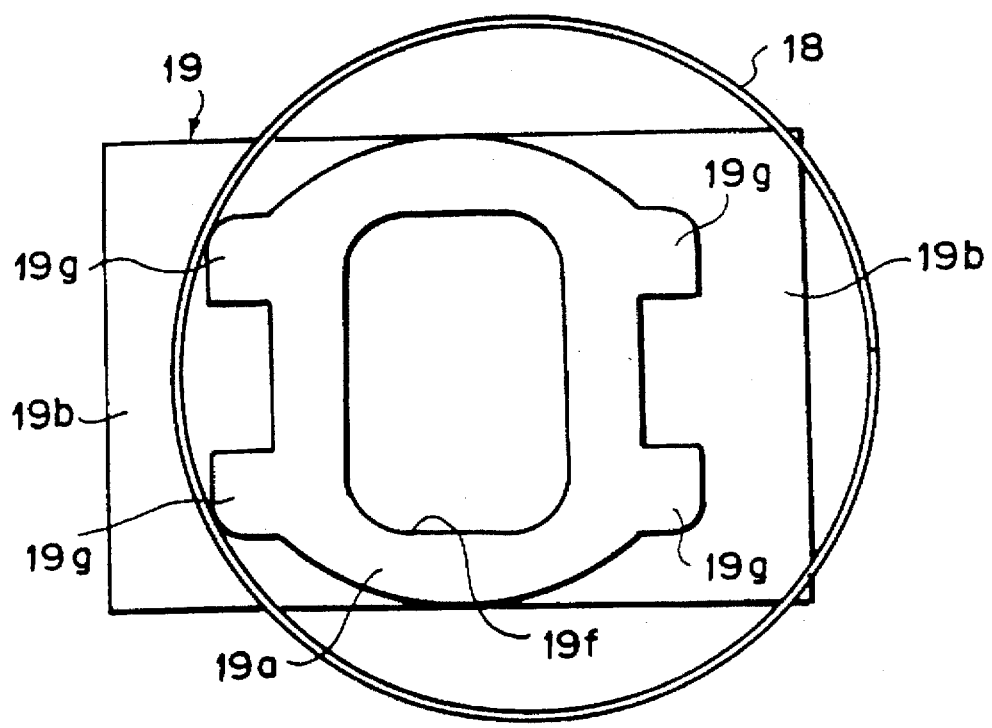
FIG. 7 is a bottom view showing a modification of the stopper and the coiled spring of the film pressing mechanism.

In the modification of the film pressing mechanism shown in FIG. 7, the slider portion 19a of the stopper 19 is provided with for limiting portions 19g which are like longitudinal ribs longitudinally extending at four corners of the slider portion 19a. That is, the limiting portions 19g shown in FIG. 7 are formed by removing an intermediate portion of each of the limiting portions 19e shown in FIG. 6. The limiting portions 19g function in the same manner as the limiting portions 19e shown in FIG. 6.

Figure 5A:
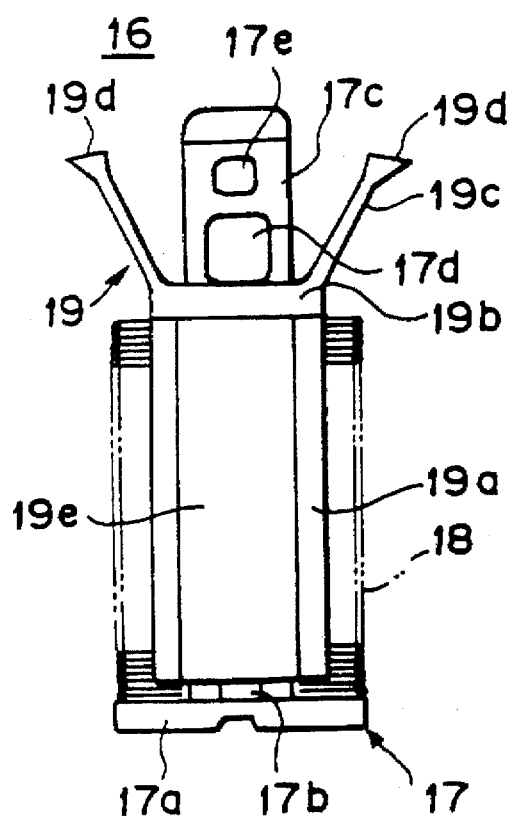
FIG. 5A is a front view of the film pressing mechanism in the assembled state.
Figure 5B:
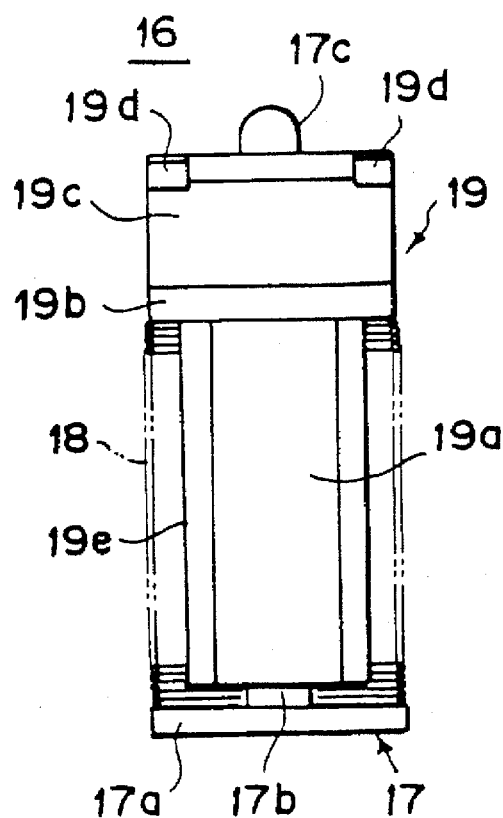
FIG. 5B is a side view of the film pressing mechanism in the assembled state.
Figure 5C:
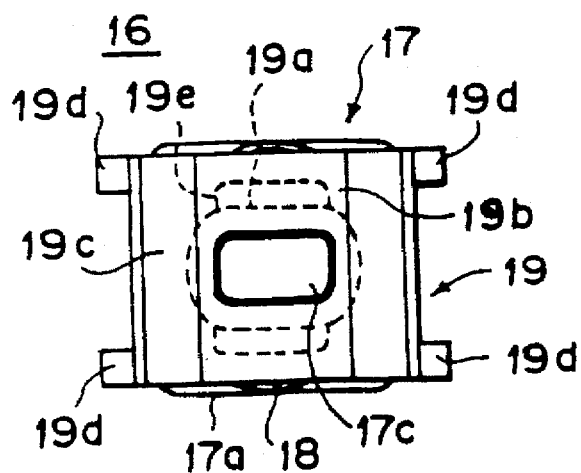
FIG. 5C is a plan view of the film pressing mechanism in the assembled state.

The coiled spring 18 is compressed between the pressing member 17a and the stopper 19 with its one end abutting against the rear face of the pressing member 17a around the shaft portion 17b and its the other end abutting against the bottom face of the spring retainer portion 19b around the slider portion 19a. Before incorporation in the cartridge body 11, the coiled spring 18 is compressed so that the holding portion 17c of the shaft portion 17b projects upward from the upper surface of the spring retainer portion 19b and a rod-like supporting portion 20b of a jig 20 (FIG. 10) to be described later is inserted into the opening 17d, whereby the film pressing mechanism 16 is united into an assembly as shown in FIG. 5A.

The film pressing mechanism assembly 16 is held by an assembly means (e.g., a robot hand) by the holding portion 17c and removed from the supporting portion 20b of the jig 20. The assembly means is provided with a part which is brought into abutment against the stopper 19 when it holds the film pressing mechanism assembly 16 by the holding portion 17c, whereby the film pressing mechanism assembly 17 is kept in the assembled state.

The length and the spring constant of the coiled spring 18 are set depending on the height of the cartridge body 11 and the height of the stack of the chemical analysis films 1 to be loaded in the cartridge body 11 so that even the last one chemical analysis film 1 can be properly pressed by the pressing member 17a even when the stopper 19 is held in the initial position relative to the cartridge body 11. For this purpose, the coiled spring 18 is given a large length and a large diameter.

The effective center of the coiled spring 18 may be aligned with the center of the spring retainer portion 19b by changing the shape of the coiled spring 18. For example, in the case of a coiled spring which is substantially annular in a cross-section taken along a plane normal to its longitudinal axis, its effective center can be aligned with the center of the spring retainer portion 19b by making smaller the diameter of the spring at one end than that in any other portion of the spring. Further the effective center of the coiled spring can be aligned with the center of the spring retainer portion 19b by shaping the spring to be a rectangle or a square having rounded corners in cross-section.

Figure 2:
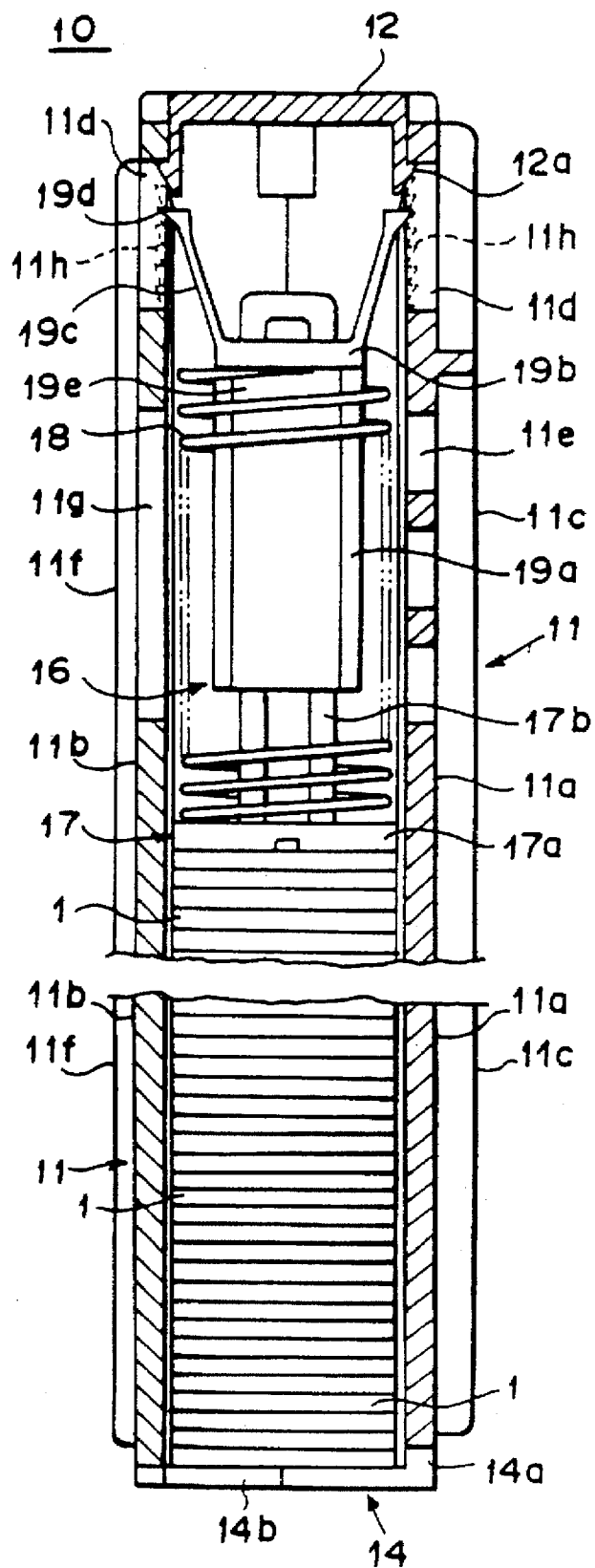
FIG. 2 is a cross-sectional view taking along line A—A in FIG. 1.
Figure 3:
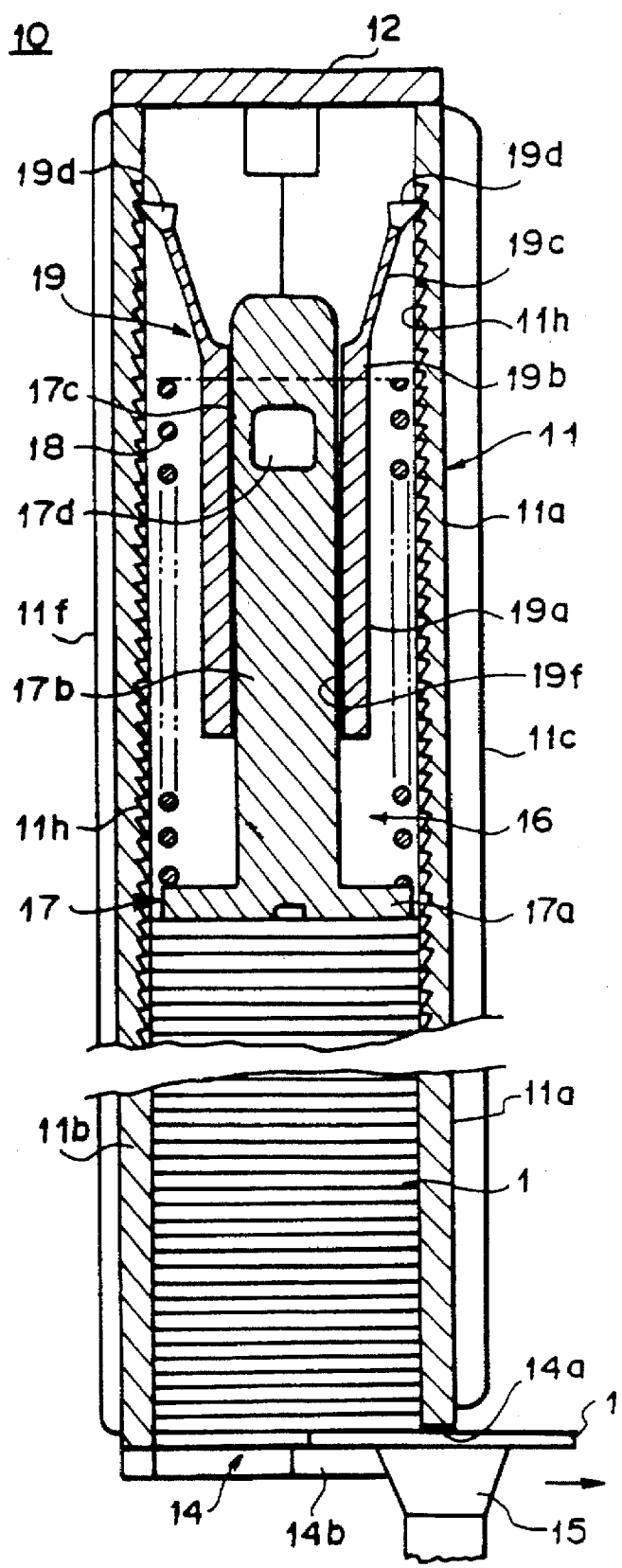
FIG. 3 is a cross-sectional view of the cartridge showing the manner of taking the chemical analysis film from the cartridge.
Figure 4:
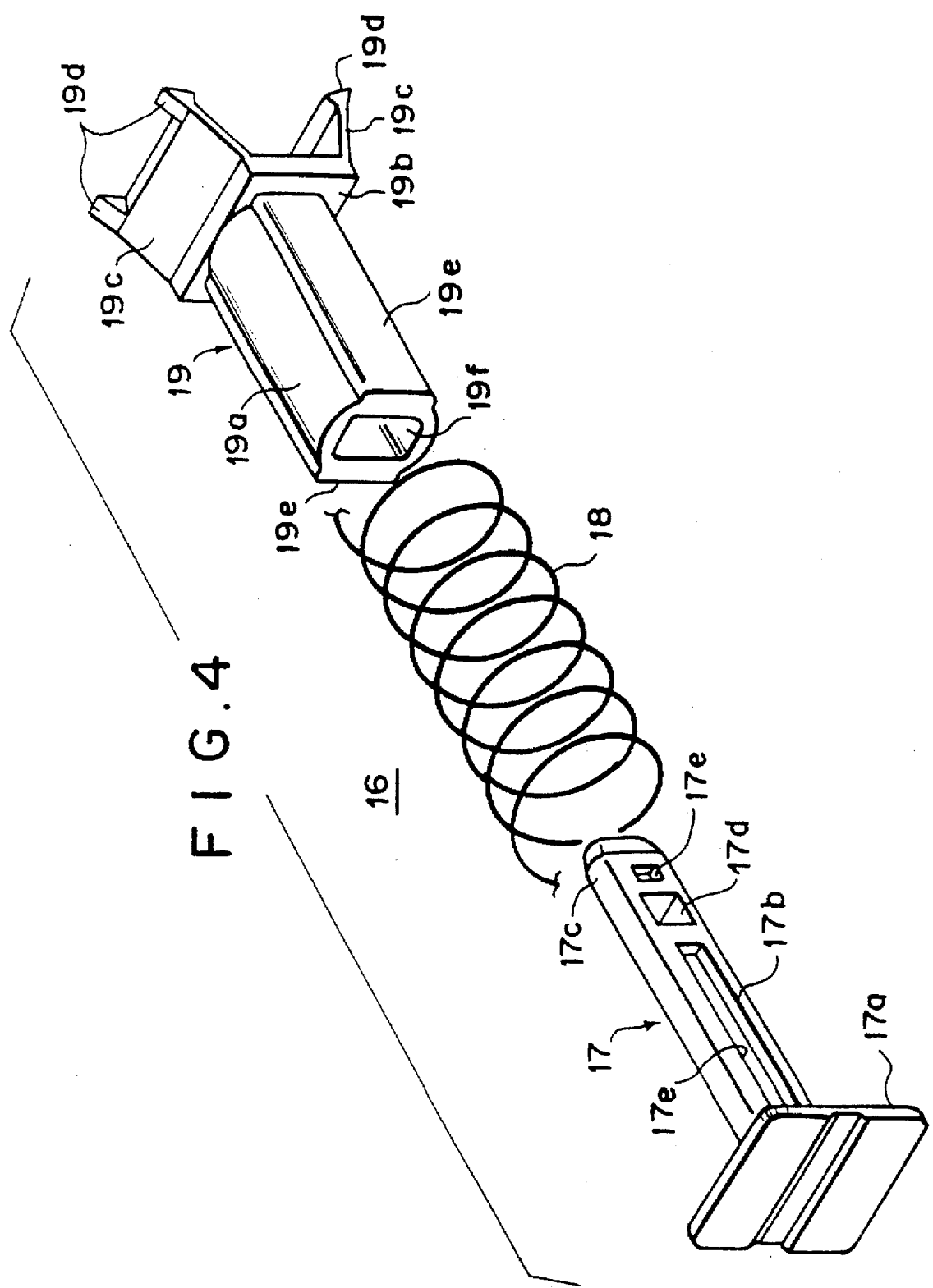
FIG. 4 is an exploded perspective view showing the film pressing mechanism employed in the cartridge.

FIGS. 2 and 3 show an initial state as a predetermined number of chemical analysis films 1 are loaded in the cartridge body 11. In the initial state, the distance by which the pressing member 17a can be moved away from the uppermost chemical analysis film 1, i.e., the distance between the upper surface of the pressing member 17a and the lower end of the slider portion 19a, is set smaller than the width of the chemical analysis film 1, whereby the chemical analysis film 1 is prevented from erecting or being reversed when the pressing member 17a is moved away from the film take-out port 14.

The initial position of the stopper 19 relative to the cartridge body 11 is changed according to the number of the chemical analysis films 1 to be loaded in the cartridge body 11 to prevent the coiled spring 18 from stretching excessively long to permit the pressing member 17a to move away from the uppermost film 1 by a distance larger than the width of the film 1.

Figure 9A:
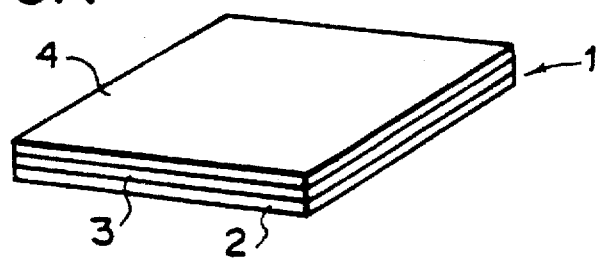
FIG. 9A is a perspective view showing a frameless chemical analysis film under the normal humidity condition.

As shown in FIG. 9A, the frameless chemical analysis film 1 to be loaded in the cartridge body 11 comprises a light-transmittive (transparent) support sheet 2 formed of plastic film or organic polymer sheet such as polyethylene terephthalate, polystyrene or the like, a reagent layer 3 and a spreading layer 4. That is, the frameless chemical analysis film 1 is formed by coating or bonding the reagent layer 3 on the support sheet 2 and laminating the spreading layer 4 on the reagent layer 3. The film 1 is not provided with any frame.

The reagent layer 3 comprises at least one layer composed of a porous layer or a hydrophilic polymer binder such as gelatin containing therein a detecting reagent component which selectively reacts with an analyte and a reagent component (chemical analysis reagent, immunoassay reagent or the like) which is necessary for coloring reaction. The spreading layer 4 is formed of a material resistant to rubbing such as woven or knitted fabric (or cloth) of synthetic fiber such as polyester or of blend of natural fiber and synthetic fiber, or paper and functions as a protective layer. Further the spreading layer 4 causes a sample liquid spotted thereon to uniformly spread over the reagent layer.

Figure 9B:
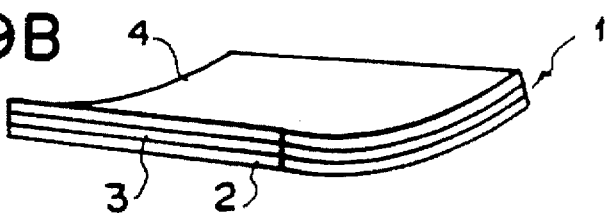
FIGS. 9B and 9C are perspective views showing the frameless chemical analysis film in a dry state.
Figure 9C:
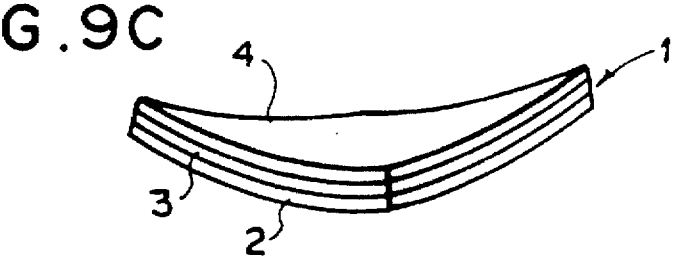

Under the normal humidity conditions, the frameless chemical analysis film 1 is substantially flat as shown in FIG. 9A. The film 1 is stored in a dry environment (e.g., in an environment where the humidity is not higher than 20%) in order to suppress chemical reaction or immunoreaction, and in a dry state, the film 1 is warped (curled or curved) toward the spreading layer 4 as shown in FIG. 9B or 9C. In the state shown in FIG. 9B, the film 1 is curled in one direction and in the state shown in FIG. 9C, the film 1 is curled in a plurality of directions.

Figure 10:
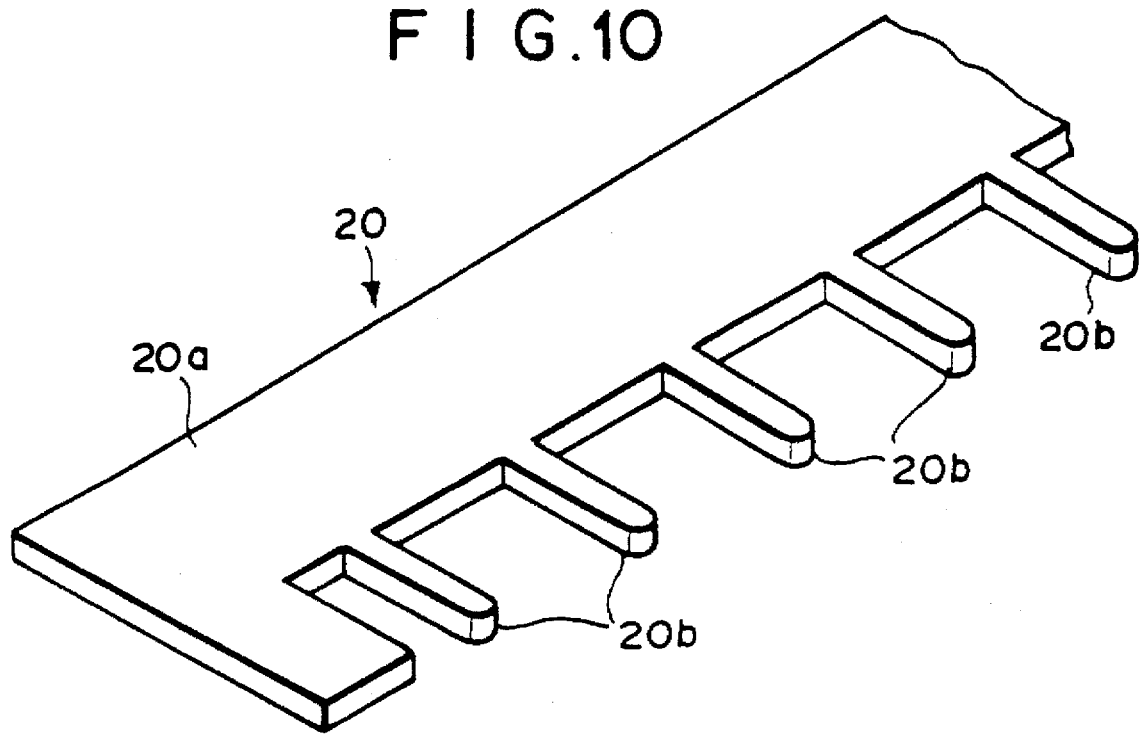
FIG. 10 is a fragmentary perspective view showing a jig for assembly of the cartridge.
Figure 11:
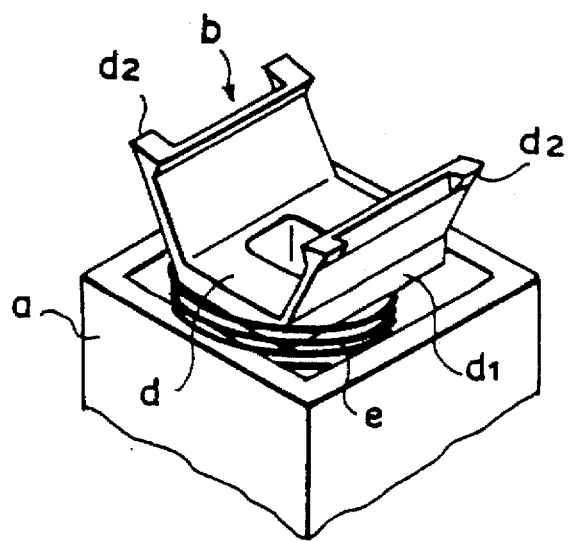
FIG. 11 is a fragmentary perspective view for illustrating trouble which can occur in the conventional chemical analysis element cartridge.

FIG. 10 shows a jig 20 for holding the film pressing mechanism assembly 17 in the assembled state in the process of preparation for incorporating the assembly 17 in the cartridge body 11. The jig 20 comprises a plate-like base portion 20a and a plurality of rod-like supporting portions 20 projecting from the base portion 20a at predetermined intervals.

Each of the supporting portions 20b is inserted into the opening 17d formed in the holding portion 17c of the shaft portion 17b with the coiled spring 18 compressed between the pressing member 17a and the stopper 19 and the holding portion 17c projecting through the stopper 19 as shown in FIG. 5A, whereby the spring 18 is kept compressed and the holding portion 17c is kept projecting through the stopper 19. In this manner, a plurality of film pressing mechanisms 16 are held on the jig 20 in a row. At this time, the limiting portion 19e on the stopper 19 limits the movement of the coiled spring 18 so that the end of the coiled spring 18 cannot be outside any one of the corners of the spring retainer portion 19b.

When assembling the frameless chemical analysis film cartridge 10, a predetermined number of ,e.g., 50 or 100, frameless chemical analysis films 1 are stacked in the cartridge body 11 through the open top end of the cartridge body 11 with the lid member 12 removed. When the frameless chemical analysis films 1 are stacked, small spaces are formed among the films 1 according to the degree or state of their curl and the stack of the films 1 has resiliency against compression.

Then the film pressing mechanism assembly 16 which has been held in the assembled state by the jig 20 is held by an assembly means (e.g., a robot hand) by the holding portion 17c and is inserted into the cartridge body 11 until the pressing member 17a is brought into abutment against the stack of the films 1 or just short of the stack while the ratchet claws 19d are brought into engagement with the ratchet teeth 11h on the cartridge body 11. Thereafter the holding portion 17c is released and the lid member 12 is mounted on the cartridge body 11. When the holding portion 17c is released, the pressing member 17a is moved downward under the force of the coiled spring 18 and presses the stack of the films 1.

Since no part of the spring 18 can protect outward beyond a corner of the spring retainer portion 19b by virtue of the limiting portion 19e, the film pressing mechanism 16 can be easily inserted into the cartridge body 11 without fear of the spring 18 being caught between the cartridge body 11 and the spring retainer portion 19b.

The chemical analysis elements to be loaded in the cartridge 10 need not be limited to the frameless chemical analysis films but may be the chemical analysis slides, the single-layered or multi-layered chemical analysis films formed of filter paper (with or without frame), the electrolyte analysis slides for quantitatively analyzing the activity of particular ionic substances contained in a sample liquid or other like elements and devices for various analyses as described above. Further the method of taking out the chemical analysis elements need not be limited to that described above where a suction pad is employed but any other suitable method can be employed. For example, the chemical analysis element may be pushed out of the cartridge body by use of a pusher blade or the like.

What is claimed is:

1. A chemical analysis element pressing mechanism for a chemical analysis element cartridge which is inserted into a cartridge body to press a stack of chemical analysis elements in the cartridge body toward an element take-out port formed in one end of the cartridge body which element pressing mechanism comprising a stopper to be engaged with an engagement means formed on an inner wall surface of the cartridge body and a pressing member which presses the stack of the chemical analysis elements toward the element take-out port under the force of a coiled spring, said stopper having a slider member which is slidable relative to a shaft portion of the pressing member which is disposed in the cartridge body to be slidable toward and away from the stack of the chemical analysis element on the side of the stack remote from the element take-out port, said coiled spring being disposed around the slider member with its one end in abutment against the pressing member and its the other end retained by a spring retainer portion formed on one end of the slider member, wherein the improvement comprises that an aligning means which aligns an effective center of an envelope defined by said the other end of the coiled spring with the effective center of the spring retainer portion is provided on the outer surface of the slider member and/or the coiled spring.

2. A chemical analysis element pressing mechanism as defined in claim 1 in which said coiled spring is substantially annular in a cross-section taken along a plane normal to its longitudinal axis and said aligning means comprises a limiting portion which is in the form of a bulged portion formed on the outer surface of the slider member.

3. A chemical analysis element pressing mechanism as defined in claim 1 in which said coiled spring is substantially annular in a cross-section taken along a plane normal to its longitudinal axis, and the diameter of the coiled spring is smaller at said the other end than that in any other portion of the spring.

4. A chemical analysis element pressing mechanism as defined in claim 1 in which said coiled spring is a rectangle or a square having rounded corners in cross-section.

* * * * *